United States Patent [19]

Ott

[11] Patent Number: 4,932,417
[45] Date of Patent: Jun. 12, 1990

[54] DEVICE FOR STABILIZING TISSUE

[76] Inventor: Douglas E. Ott, 4309 Old Club Rd., Macon, Ga. 31210

[21] Appl. No.: 219,253

[22] Filed: Jul. 15, 1988

[51] Int. Cl.⁵ .............................................. A61B 10/00
[52] U.S. Cl. ...................................... 128/749; 128/757
[58] Field of Search ............... 128/341, 345, 749, 751, 128/754, 756–757, 305; 604/54–55, 104–109

[56] References Cited

U.S. PATENT DOCUMENTS

| Re. 32,275 | 11/1986 | Zartman | 128/345 X |
| 2,541,691 | 2/1951 | Eicher | 128/345 X |
| 3,467,090 | 9/1969 | Zollett | 604/107 X |
| 3,472,231 | 10/1969 | Niebel et al. | 128/341 |
| 4,273,131 | 6/1981 | Olsen | 128/341 |
| 4,557,255 | 12/1985 | Goodman | 128/345 X |
| 4,654,028 | 3/1987 | Suma | 128/345 X |
| 4,785,826 | 11/1988 | Ward | 128/754 |

*Primary Examiner*—Angela D. Sykes
*Attorney, Agent, or Firm*—Needle & Rosenberg

[57] ABSTRACT

The present invention is a device for stabilizing tissue during surgery having an elongated sheath, a rod movable within the sheath and having a forward end capable of being extended beyond the sheath, and tissue grasping prongs located at said forward end of said rod, said prongs extending laterally away from said rod when said forward end is extended beyond the sheath for impinging and stabilizing tissue.

6 Claims, 2 Drawing Sheets

DEVICE FOR STABILIZING TISSUE

BACKGROUND OF THE INVENTION

The present invention relates to a surgical device, and more particularly to a device for stabilizing endocervical tissue during cold knife or laser conization.

Conization is a surgical procedure involving the excision of a cone of endocervical tissue with a cold knife blade or laser for pathological examination. An important consideration during such procedure is the avoidance of any charring or other compromising of the tissue during removal so that the histological characteristics of the tissue are preserved. Most importantly, the tissue comprising the outermost ring of the removed mass must be undamaged, since this is what is examined to determine the extent to which cancer or other disease has spread. The methods presently used to stabilize the tissue during conization however, are contrary to this consideration.

Currently, the endocervical tissue is stabilized during conization by grasping the outermost edges of the tissue mass with a pincher or a long skin hook. As the excision is performed, the grasping is alternated along the edge of the mass, or cone. This grasping results in compromise to the tissue, and can lead to the masking of otherwise detectable histological characteristics.

Therefore, there exists a need for a device which can be used for stabilizing and removing tissue during conization without damage to the tissue.

There exists a further need for such a device which is quick and easy to use, which has a minimum of parts, and which can be inexpensively produced.

SUMMARY OF THE INVENTION

The above-mentioned considerations are met by the present invention, which relates to a device for stabilizing tissue during conization. The device is comprised of an elongated, tubelike sheath having an opening at each end and surrounding a plunger rod. Attached to the forward end of the plunger rod are a plurality of prongs which are in a spaced apart relationship. Each prong is outwardly bent and has a downwardly extending tip on its distal end. In the device's retracted position, the rearward end of the plunger rod extends beyond the sheath and the prongs are held inside the sheath. This allows easy insertion of the device into the vagina so that the forward end of the sheath is surrounded by the cervical tissue to be removed. Once positioned, the device is placed into extended position by pushing the plunger rod forward through the sheath so that the forward end of the rod and the prongs are exposed. Subsequent pulling the rod rearward results in the prongs impinging the tissue, and conization can be performed. Once the tissue mass is freed, the mass is removed from the vagina by withdrawal of the device.

It should be seen, therefore, that the present device minimizes contact with the tissue, and particularly avoids contact with the important outermost edge of the cone. Rather, the prongs, once imbedded in the tissue, hold the tissue stable during the procedure and the need to change grasping positions is eliminated.

Furthermore, the number and the positioning of the prongs may be altered to enable the tissue to be grasped only at predetermined points in the cervix. This is useful when, for example, examination with a colposcope has shown a particular area to be worthy of special considerations.

In is an object of the present invention, therefore, to provide a device which can be used to stabilize and remove tissue during conization with minimal damage to the tissue.

It is also an object of the present invention to provide such a device which allows the surgeon to predetermine the point of impingement of the stabilizing and removing device.

It is a further object of the present invention to provide such a device which is quick and easy to use, which has a minimum of parts, and which can be inexpensively produced.

These and other objects and advantages may be seen from the following detailed description of a preferred embodiment of the invention.

DETAILED DESCRIPTION OF THE ILLUSTRATIVE EMBODIMENT

The present invention is described below with reference to the drawings, in which like numbers indicate like parts throughout the views.

Figure 1:
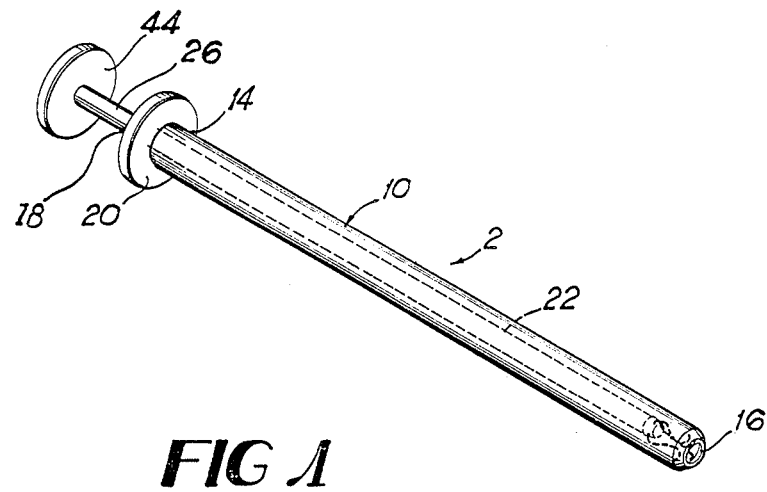
FIG. 1 is a perspective view of the device of the present invention.

Referring to FIG. 1, a device 2 for stabilizing tissue during cold knife or laser conization is shown. The device 2 is comprised of an elongated sheath 10 which is tubular and has a forward inwardly directed end 12 with opening 16 and a rearward end 14 with corresponding opening 18. The surface of the sheath 10 can be either blackened, dulled or otherwise made to decrease the reflection of electromagnetic energy for safety purposes. The forward end 12 may be tapered for aiding in the insertion of the device 2 into the cervix, as discussed more fully below. An end cap 20 is provided at the rearward end 14 of the sheath 10 for aiding in manually gripping the device 2.

An elongated plunger rod 22 is housed within and guided by the sheath 10. The rod 22 terminates in a forward end 24 that is frusto-conical in shape to correspond to the forward end 12 of the sheath 10 and a rearward end 26 which corresponds to the rearward end of the sheath 10 when the rod 22 is within the sheath 10. A plate 44, is provided on the rearward end 26 of the rod 22 for alternately pushing and pulling the rod 22.

Figure 2:
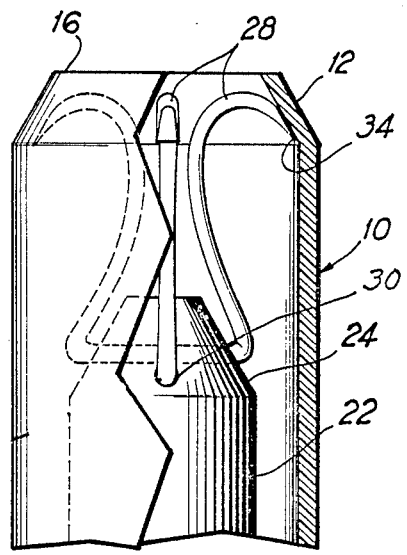
FIG. 2 is a side elevational view of the forward end of the device of the present invention in retracted position.
Figure 4A:
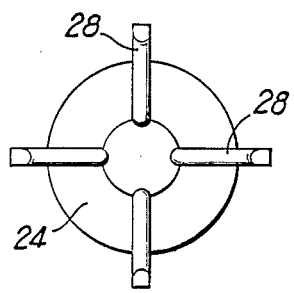
FIG. 4 A-C are top views of alternate embodiments of the prong positions of the device of the present invention when the device is in its operational position.
Figure 4B:
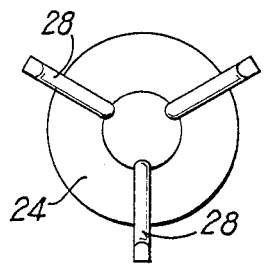
Figure 4C:
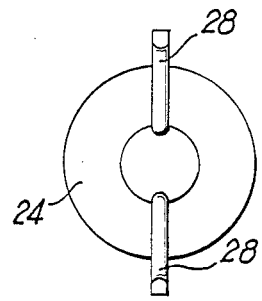

A plurality of tissue grasping means or prongs 28 are located on and extend from the forward end 24 of the rod 22. As seen in FIG. 2, the prongs 28 may be either connectingly placed through holes 30 in the rod 22, welded or otherwise firmly attached to the rod 22. The prongs 28 are preferably made of, but not limited to, tempered copper or stainless steel wire. As seen in FIGS. 4A-C, any number of prongs 28 may be utilized, preferably being in a spaced apart relation to one another, depending upon the nature of the task desired to be performed. For example, FIG. 4A shows four prongs 28 being at 90° intervals to each other; FIG. 4B shows three prongs 28 spaced apart at 120° intervals; and FIG. 4C shows two prongs 28 at 180° intervals. The even spacing of the prongs 28 enhances impingement during a conization procedure, and also enables the surgeon to choose the extent and location of contact with the tissue.

Figure 3:
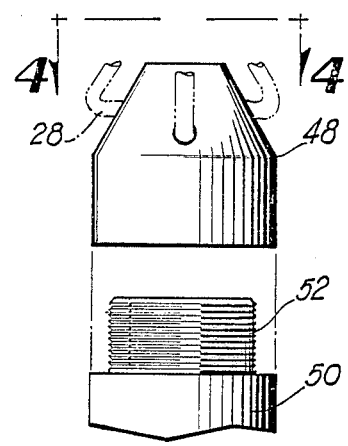
FIG. 3 is a side elevational view of an alternate embodiment of the forward end of the plunger rod of the device of the present invention.

The rod 22 may be of a unitary construction, as shown in FIG. 2, or as shown in FIG. 3, may be comprised of a cap 48 attachable to a rod shaft 50 by threaded connecting means 52. The use of interchangeable caps 48 and connecting means 52 enables the device 2 to be reused with different numbers of prongs 28, if desired.

Each prong 28 is bent along its body to terminate in a downwardly directed tip 34 so as to approximate the numeral "2" in profile. The prongs 28 are of a flexible construction so that they are moved toward the longitudinal axis of the rod 22 when the device is in its retracted, inoperable position as shown in FIG. 2. When the rod 22 is pushed outwardly from the sheath, the prongs 28 spring to an extended, operative position as shown in FIG. 5B.

Figure 5A:
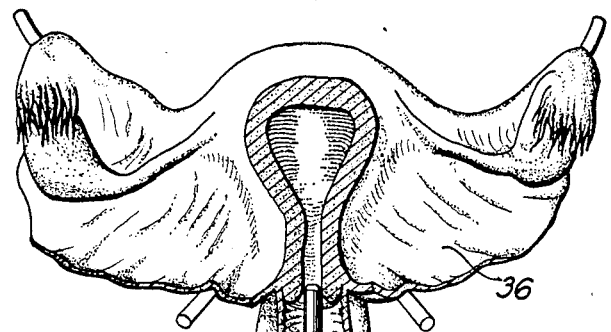
FIG. 5 A-D are partial cross-sectional views of a human cervix during a conization procedure using the device of the present invention.
Figure 5B:
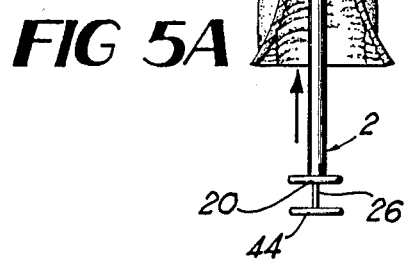
Figure 5B:
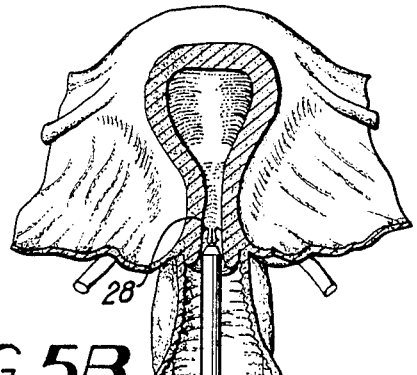
Figure 5C:
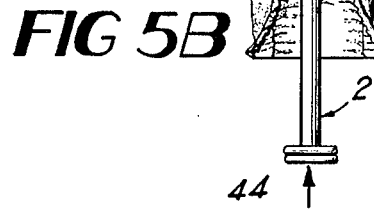
Figure 5C:
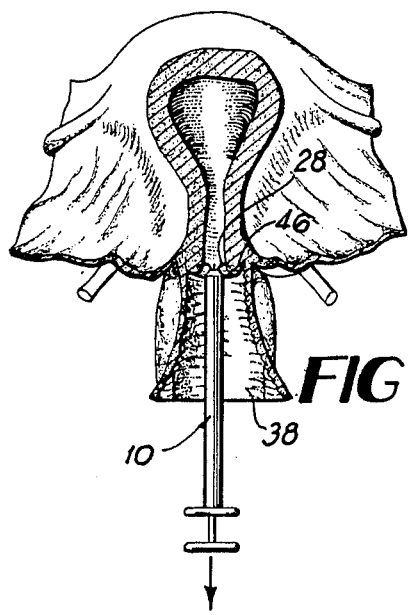
Figure 5D:
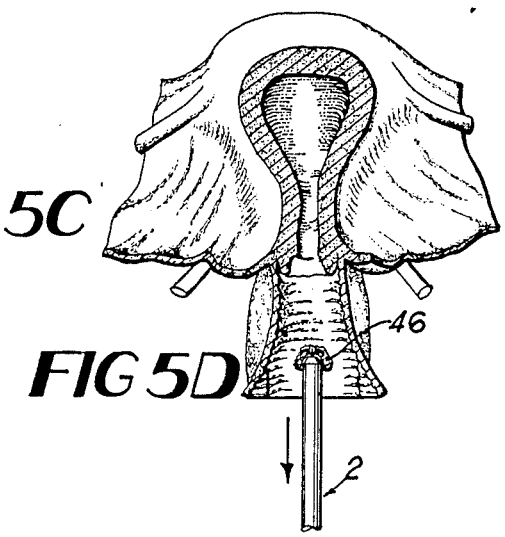

FIGS. 5A-D illustrate the use of the present device 2 during the removal of tissue from a cervix 36. As shown in FIG. 5A, the device 2, with its prongs 28 in a retracted position within the sheath 10, is inserted into the vagina 38 so that the forward end 12 enters the endocervical canal. The rod 22 is then moved forward through the sheath 10 by pushing on the plate 44, so that the prongs 28 exit the sheath 10 and move outwardly toward the surrounding tissue as shown in FIG. 5B. The rod 22 is then retracted through the sheath 10 by pulling on the plate 44, as shown in FIG. 5C. The retraction of the rod 22 results in a corresponding retraction of the prongs 28, which grasp and impinge the surrounding endocervical canal tissue 46. Cold knife or laser conization is then performed to excise the tissue 46 from the remainder of the cervix 36. As shown in FIG. 5D, the excised tissue 46 may be removed from the patient by withdrawal of the device 2 from the vagina 38. Once the tissue 46 has been obtained, the device 2 can be thrown away.

A modification of the device 2 may have a handle on sheath 10 which would be offset to allow better visualization of the tissue 46 being removed.

What is claimed is:

1. A device for inserting into a body cavity for stabilizing and removing tissue with minimal compromise during surgery comprising:
   (a) an elongated sheath;
   (b) a rod movable within said sheath and having a forward end capable of being extended beyond said sheath; and
   (c) a plurality of resilient prongs each having a sharp tip directed laterally away from said rod and downwardly towards said sheath located at said forward end of said rod, said means initially housed within said sheath to minimize compromising said tissue when said device is inserted into said body cavity and capable of extending laterally away from said rod when said forward end is extended beyond said sheath and impinging into said tissue upon retraction of said device from said body cavity.

2. The device of claim 1, wherein said device comprises a plurality of said tissue grasping means.

3. The device of claim 2, wherein there are provided two grasping means in opposing relationship with each other for use in a conization procedure.

4. The device of claim 2, wherein said grasping means are evenly spaced for use in a conization procedure.

5. The device of claim 1, wherein said sheath has a frusto-conical forward end for holding said prong in biased position within said sheath prior to extension of said forward end of said rod.

6. The device of claim 1, wherein said rod is longer than said sheath so that the rearward end of said rod extends beyond said sheath when said tissue grasping means are held within said sheath, said rod forward end and said prong capable of being extended out of said sheath by moving said rearward end of said rod towards said sheath.

* * * * *